(12) United States Patent
Hudlicky et al.

(10) Patent No.: US 6,242,604 B1
(45) Date of Patent: Jun. 5, 2001

(54) PROCESS FOR PREPARING A MORPHINAN DERIVATIVE

(75) Inventors: Tomas Hudlicky; Gabor Butora, both of Gainesville, FL (US)

(73) Assignee: Mallinckrodt Inc., St. Louis, MO (US)

( * ) Notice: Subject to any disclaimer, the term of this patent is extended or adjusted under 35 U.S.C. 154(b) by 6 days.

(21) Appl. No.: 09/636,633

(22) Filed: Aug. 11, 2000

Related U.S. Application Data

(62) Division of application No. 09/256,332, filed on Feb. 19, 1999, now Pat. No. 6,136,979, which is a continuation of application No. 03/939,245, filed on Sep. 29, 1997, now Pat. No. 5,912,347.
(60) Provisional application No. 60/027,494, filed on Sep. 30, 1996.

(51) Int. Cl.$^7$ ................... C07D 498/02; C07D 413/02; C07D 491/12
(52) U.S. Cl. ................... 546/92; 548/229; 546/42; 546/48
(58) Field of Search ................... 548/229; 546/42, 546/48, 92

(56) References Cited

U.S. PATENT DOCUMENTS

| | | | |
|---|---|---|---|
| 5,912,347 | * | 6/1999 | Hudlicky et al. ................ 546/44 |
| 5,952,495 | * | 6/1999 | Huang et al. ................ 544/125 |

OTHER PUBLICATIONS

Butora, G. et al. : Chemoenzymatic synthesis of the morphine skelton via radical cyclization and a C10–C11 closure. Tetrahed. Lett. vol. 37, pp. 8155–8158, Nov. 4, 1996.*
Arthur G.Schultz et al.Journal of Org.Chem.,vol. 50, pp. 217–231, 1985.*
Kathlyn A. Parker et al., "The Radical Cyclization Approach to Morphine, Models for Highly Oxygenated Ring–III Synthons",*J. Org. Chem.*, vol. 59, No. 14, 1994, pp. 3933–3938.

* cited by examiner

*Primary Examiner*—C. S. Aulakh
(74) *Attorney, Agent, or Firm*—Rothwell, Figg, Ernst & Manbeck

(57) ABSTRACT

A process for preparing a morphinan derivative, by providing a dihydrofuranyl bridged tetracycle halide of the formula (19)

(19)

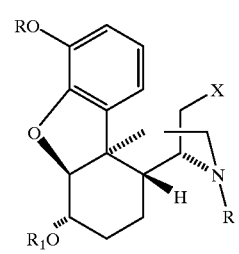

wherein X is halogen, R is an alkyl group of from 1 to about 10 carbon atoms, and $R_1$ is a protecting group; and converting the pentacycle halide into a morphinan derivative of formula (20)

(20)

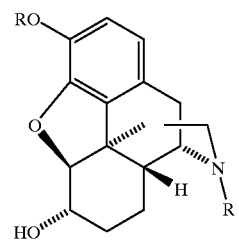

wherein R is as defined above.

7 Claims, No Drawings

PROCESS FOR PREPARING A MORPHINAN DERIVATIVE

CROSS-REFERENCE TO RELATED APPLICATION

This application is a divisional of U.S. patent application Ser. No. 09/256,332, filed Feb. 19, 1999, allowed, now U.S. Pat. No. 6,136,979, which is a continuation of U.S. Ser. No. 08/939,245, filed Sep. 29, 1997, now U.S. Pat. No. 5,912,347, which claims priority from provisional application Serial No. 60/027,494, filed Sep. 30, 1996.

FIELD OF THE INVENTION

The present invention relates to the field of morphinans.

DESCRIPTION OF THE BACKGROUND ART

In 1954, Gates reported the first total synthesis of morphine 1 by an ingenious yet simple route, utilizing a β-dihydrothebainone-dihydrothebainone isomerization sequence in order to adjust the $C_{14}$ stereocenter. Since Gates's original approach, a total of 16 syntheses have been reported. The majority (nine of them), including the most recent one of Overman, proceed via 1-benzylisoquinoline intermediates, with the crucial step being $C_{12}$–$C_{13}$ bond formation. These syntheses are formalized by intercepting Gates's dihydrothebainone (or βdihydrothebainone) or by producing thebaine. The most efficient routes to date, those of Rice and Beyerman, have also used this strategy. Despite a number of attempts, only one successful synthesis (Evans) utilized a $C_{10}$–$C_{11}$ closure late in the synthesis in order to complete the morphinan skeleton, followed by adjustment of stereochemistry at $C_{14}$.

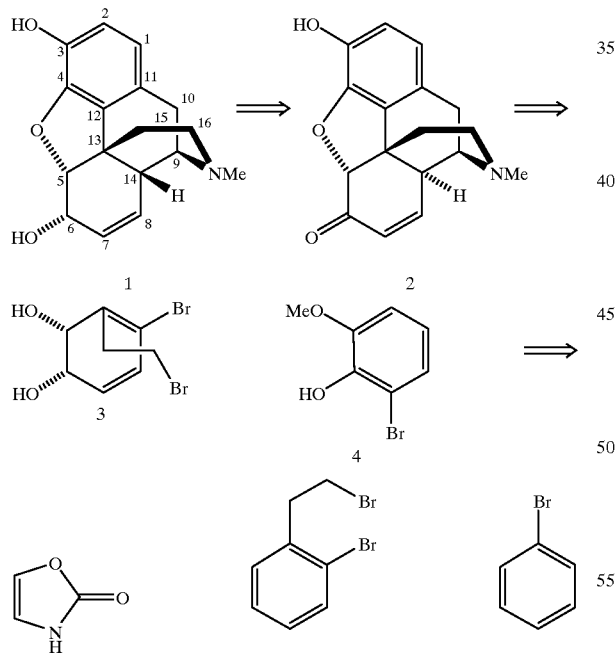

In 1994, Parker reported the full details of a radical cascade approach (published in a preliminary form in 1992) to racemic 1.

SUMMARY OF THE INVENTION

A process for preparing a morphinan derivative, by providing a dihydrofuranyl bridged tetracycle halide of the formula (19)

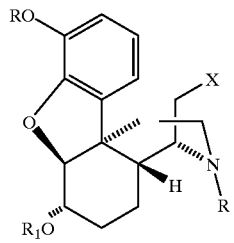

(19)

wherein X is halogen, R is an alkyl group of from 1 to about 10 carbon atoms, and $R_1$ is a protecting group; and converting the pentacycle halide into a morphinan derivative of formula (20)

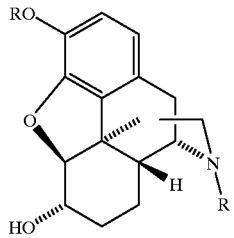

(20)

wherein R is as defined above.

DESCRIPTION OF THE PREFERRED EMBODIMENTS

In accordance with one embodiment, the invention is directed to a process for preparing a morphinan derivative, comprising providing a dihydrofuranyl bridged tetracycle halide of the formula (19)

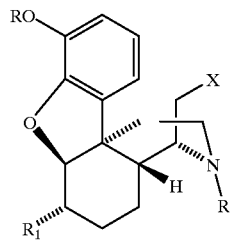

(19)

wherein X is halogen, R is an alkyl group of from 1 to about 10 carbon atoms, and $R_1$ is a protecting group; and converting said pentacycle halide into a morphinan derivative of formula (20)

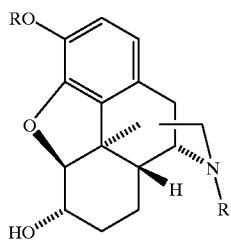

(20)

wherein R is as defined above. In preferred embodiments, X is chlorine (Cl) and R is methyl. In further preferred embodiments, tetracycle halide is provided by converting a tetracycle of the formula (18)

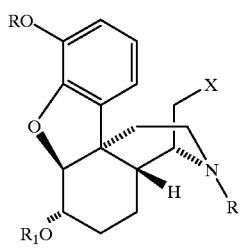

(18)

wherein X is OH, and wherein R and R₁ are as defined above, into said tetracycle halide.

In preferred embodiments, said tetracycle is exposed to a methane sulfonyl halide and triethylamine, so as to convert said tetracycle to said tetracycle halide.

In further preferred embodiments, said tetracycle is provided by reducing a protected pentacycle of the formula (13)

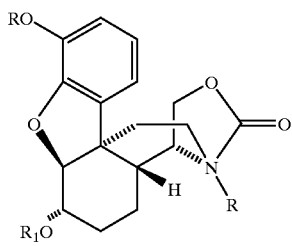

(13)

wherein R and R₁ are as defined above, so as to form said tetracycle.

In preferred embodiments, said protected pentacycle is reduced with diisobutyl aluminum hydride in the presence of methylene chloride. In further preferred embodiments, said protected pentacycle is provided by cyclizing an aromatic halide of the formula (12)

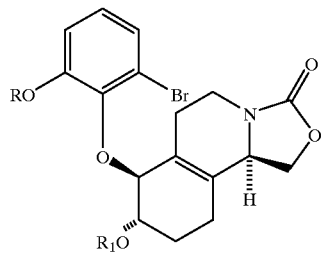

(12)

wherein R and R₁ are as defined above, so as to form said protected pentacycle.

In preferred embodiments, said aromatic halide is cyclized in the presence of tributyltin hydride, azobisisobutyronitrile and benzene so as to convert said aromatic halide to said protected pentacycle. In further preferred embodiments, said aromatic halide is provided by protecting an acetonide of the formula (11a)

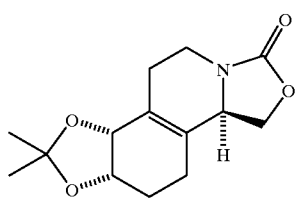

(11a)

to form a diol of the formula (11a₁)

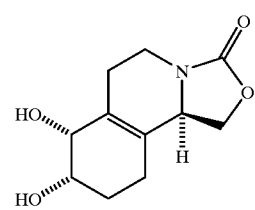

(11a₁)

and converting said diol into said aromatic halide by displacement of OH.

In preferred embodiments, said protected diol is reacted with the monomethyl ether of the bromocatechol of formula (4)

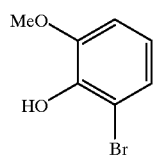

(4)

so as to convert the said protected diol to said aromatic halide of formula (12). In further preferred embodiments, said diol is provided utilizing a vinyl bromide of the formula (10)

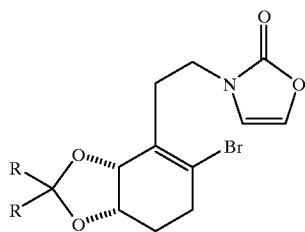

(10)

wherein R is as defined above, so as to form said diol.

In preferred embodiments, said vinyl bromide is provided by converting a diol of the formula (7)

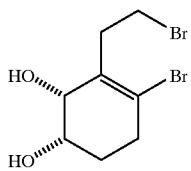

(7)

into said vinyl bromide. In further preferred embodiments, the method further includes the step of coupling to said diol an oxazolone of formula (5)

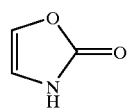

(5)

so as to convert said diol to said vinyl bromide.

In preferred embodiments, said diol is provided by reducing a diol of the formula (3)

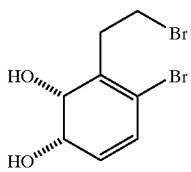

(3)

so as to convert said diol of formula (3) to said diol of formula (7). In further preferred embodiments, said diol of formula (3) is provided by conversion of an aromatic compound of the formula (6)

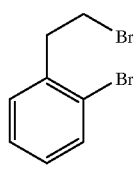

(6)

so as to form said diol of formula (3).

In accordance with one embodiment, a morphinan precursor is prepared by providing a bromobenzene of the formula (6)

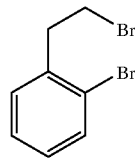

(6)

and converting said bromobenzene into a cylcohexadiene cis-diol of the formula (3)

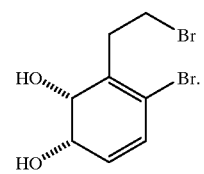

(3)

The invention is further directed to compounds selected from the group consisting of a compound of the formula (10)

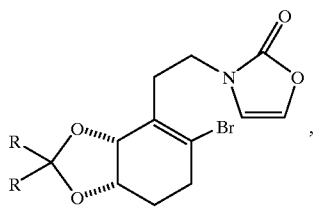

(10)

a compound of the formula (11a)

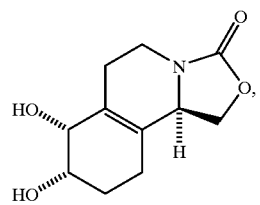

(11a)

a compound of the formula (11b)

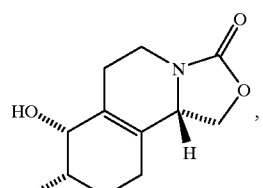

(11b)

a compound of the formula (12)

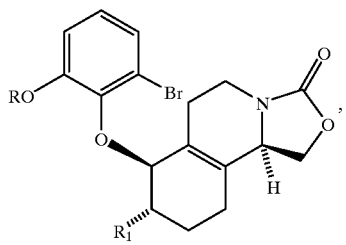
(12)

a compound of the formula (13)

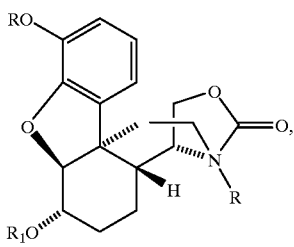
(13)

a compound of the formula (14)

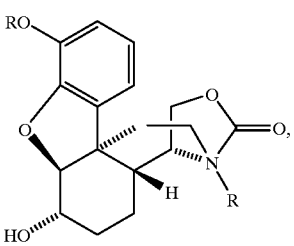
(14)

a compound of the formula (15)

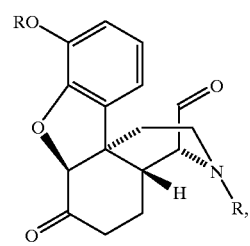
(15)

a compound of the formula (16)

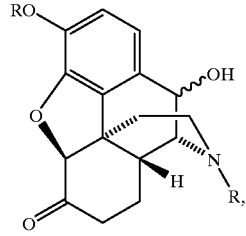
(16)

a compound of the formula (18)

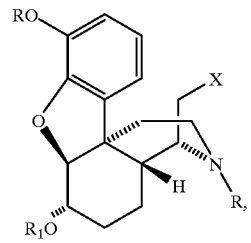
(18)

and a compound of the formula (20)

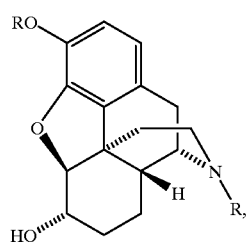
(20)

wherein R is an alkyl group of from 1 to about 10 carbon atoms, $R_1$ is a protecting group, and X=OH or halogen.

In accordance with one embodiment, the inventive compound is of the formulae (10), (12), (13), (14), (15), (16) or (20), and R is methyl.

In accordance with one embodiment, the inventive compound is of the formula (18), where R is methyl and X is OH.

In accordance with one embodiment, the inventive compound is of the formula (18), wherein R is methyl and X is Cl.

EXAMPLE

Our strategy is based on the exploitation of microbial dioxygenase-mediated degradation of toluene, elucidated by Gibson in 1969. In the arene degradation pathway, elimination of catechol dehydrogenase synthesis by mutation of the wild strain yields an organism *Pseudomonas putida* 3911/D that converts aromatic compounds to cyclohexadiene cis-diols, which accumulate in the fermentation broth. We have taken advantage of this process by converting 2-(2-bromoethyl)bromobenzene 6 to diol 3. Even though 2-bromo-6-methoxyphenol 4 is directly available via bromination of guaiacol, we have shown that the precursor, catechol 8, is also accessible from bromobenzene via full biooxidation of bromobenzene (Pp TGO2C or *E. coli* JM 109, pDTG602, where both toluene dioxygenase and catechol dehydrogenase are expressed) or partial biooxidation (Pp 39/D; Jones oxidation). Exhaustive methylation (MeI/$K_2CO_3$) followed by selective demethylation (TMSI) yields 4, Scheme 1. In this fashion two of the three fragments required for synthesis are available via biocatalysis; the third, oxazolone 5, is prepared electrochemically, thus contributing to the environmentally benign nature of the synthesis.

route using the more abundant 11a, leading ultimately to ent-morphinan skeleton.

Diol 11a was selectively protected with TBDMSOTf (86%) and subjected to Mitsunobu protocol using the monomethyl ether of bromocatechol 4 to yield 12 (94%), which contains all of the carbons for codeine. This material smoothly cyclized to 13 (49%). The combined yields of both ring closures were higher than those of the radical cascade from the first generation, and the second cyclization proceeded stereospecifically giving only the diastereomer 13. The absolute stereochemistry at $C_{14}$ corresponds to that of the enantiomer of βthe bain one. The closure of the free Scheme 1

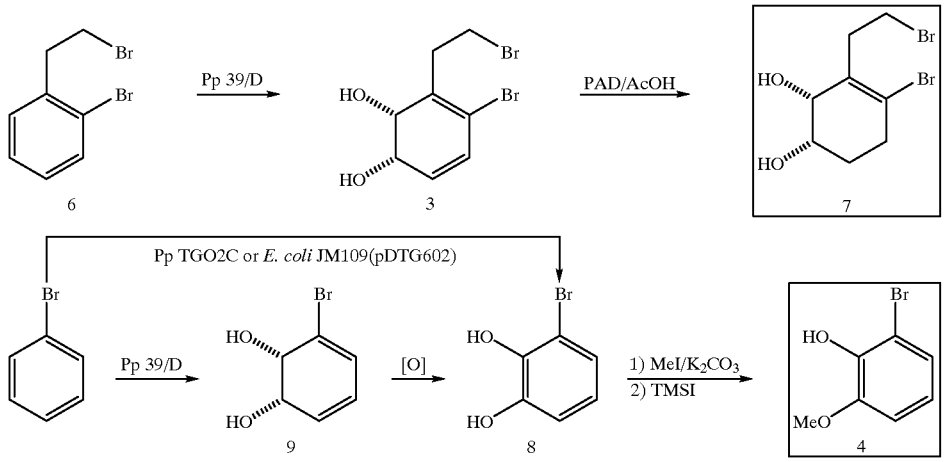

The chirality, set enzymatically in 3, is propagated though the synthesis by the directing effects of the cis-diol moiety. Diol 3 ($t_{1/2}$=one week in $CDCl_3$ solution) was reduced with dumide (50% yield) in order to minimize the tendency toward aromatization, protected as an acetonide (2,2-dimethoxy propane, methylene chloride, cat. pTsOH, 95%), and coupled with oxazolone 5 (39%) to give the precursor to the first radical closure, vinyl bromide 10. Exposure of this material to $Bu_3SnH$ and AIBN in refluxing benzene gave a 2:1 mixture of 11a and 11b in a combined yield of 89% after deprotection of the acetonide with Dowex 50×8-100 acidic resin in aqueous methanol. $^1H$- and $^{13}C$-NMR analysis and nOe, confirmed by x-ray of 11a, led to the assignment of absolute stereochemistry as shown. As the only center in morphine not subject to facile manipulation is $C_9$ corresponding to $C_1$ in isoquinolines 11, we chose to pursue the alcohol, derived from 12, did not affect the absolute stereochemistry of $C_{14}$, and the pentacyle 14 was isolated in 29% yield.

The TBDMS protected pentacycle 13 was reduced with DIBAL to 18 (95%) to furnish the N-methyl functionality and to establish the $C_{10}$ eletrophilic center by mesylation with in situ displacement to 19 (81%). Exposure of 19 to $AlCl_3$ in benzene gave material whose analysis suggested a mixture of morphinan 20 and the corresponding free phenol resulting from the aluminum-chloride-catalyzed demethylation. To our knowledge this would be the first instance of a direct $C_{10}$–$C_{11}$ closure of a compound already containing the furan ring and a $C_{10}$ $sp^3$-hybridized center. Poor reproducibility of this reaction on small scale (<5 mg) compelled us to search for alternatives.

Scheme 2

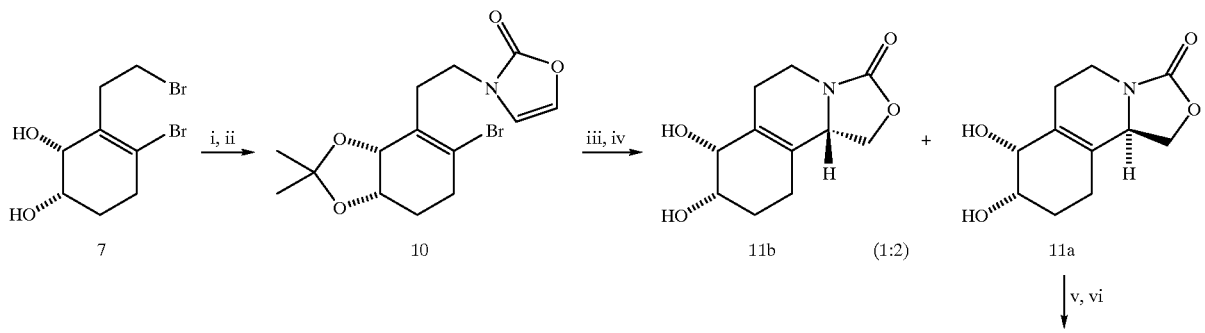

-continued

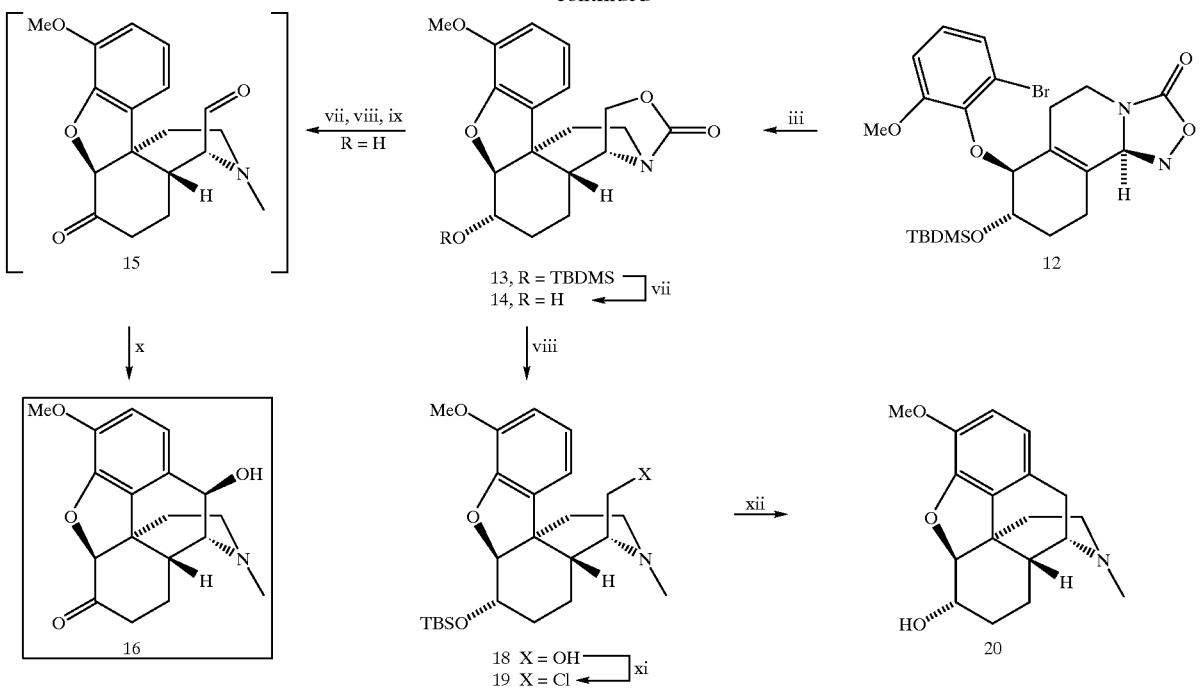

Reagents and conditions: (i) DMP, p-TSA; (ii) 5, NaH, DMSO; (iii) ⁿBu₃SnH, AIBN, benzene, reflux; (iv) Dowex 50X8-100, MeOH, H₂O; (v) TBDMSOTf, $^i$Pr₂EtN, THF, -78° C.; (vi) 4, DEAD, ⁿBu₃P, THF, 0° C.; (vii) TBAF, THF; (viii) DIBAL-H, CH₂Cl₂, 0° C.; (ix) ClCOCOCl, DMSO, Et₃N, CH₂Cl₂, -78 to 0° C.; (x) CF₃SO₃H; (xi) MsCl, Et₃N, THF; (xii) AlCl₃, benzene, reflux.

Reduction of 14 with DIBAL-H followed by a double Swern oxidation yielded the ketoaldehyde 15 (70%), which upon exposure to trifluoromethyl sulfonic acid furnished the $C_{10}$-hydroxy morphinan 16 (70%), as evidenced by the appearance of two upfield doublets, (δ6.84, 6.68 in benzene-d6, or 6.97, 6.79 in chloroform-d), corresponding to the aromatic protons of a complete morphinan skeleton. Reduction of 16, epimerization at $C_{14}$ based on a known procedure, and demethylation would formalize the synthesis of ent-morphine.

In summary, the synthesis of a complete morphinan skeleton has been accomplished with reasonable stereoselectivity in 13 steps from 2-(2-bromoethyl)bromobenzene.

What is claimed is:

1. A compound selected from the group consisting of a compound of the formula (10)

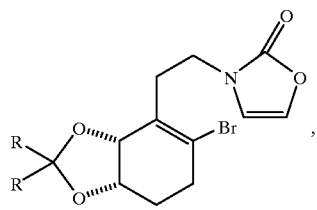

(10)

a compound of the formula (11a)

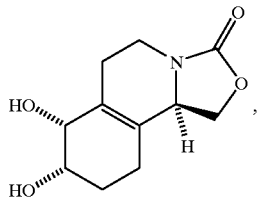

(11a)

a compound of the formula (11b)

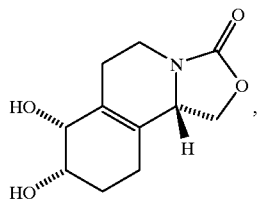

(11b)

a compound of the formula (12)

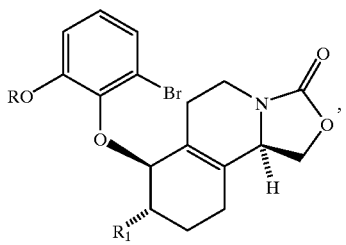
(12)

a compound of the formula (13)

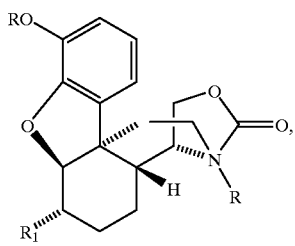
(13)

a compound of the formula (14)

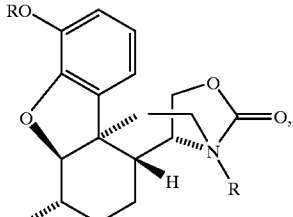
(14)

wherein R is an alkyl group of from 1 to about 10 carbon atoms and $R_1$ is a protecting group.

2. The compound of claim 1, wherein said compound is of the formula (10), and R is methyl.

3. The compound of claim 1, wherein said compound is of the formula (11a).

4. The compound of claim 1, wherein said compound is of the formula (11b).

5. The compound of claim 1, wherein said compound is of the formula (12), wherein R is methyl.

6. The compound of claim 1, wherein said compound is of the formula (13), wherein R is methyl.

7. The compound of claim 1, wherein said compound is of the formula (14), wherein R is methyl.

* * * * *

UNITED STATES PATENT AND TRADEMARK OFFICE
CERTIFICATE OF CORRECTION

PATENT NO. : 6,242,604 B1  
DATED : June 5, 2001  
INVENTOR(S) : Hudlicky et al.

Page 1 of 1

It is certified that error appears in the above-identified patent and that said Letters Patent is hereby corrected as shown below:

<u>Title page,</u>  
Under the "Related U.S. Application Data" section, in line 3, please replace "03/939,245" with -- 08/939,245 --.

Signed and Sealed this

Eighth Day of January, 2002

Attest:

JAMES E. ROGAN  
*Attesting Officer*  *Director of the United States Patent and Trademark Office*